US005572800A

United States Patent [19]
West

[11] Patent Number: 5,572,800
[45] Date of Patent: Nov. 12, 1996

[54] AIR FRESHENER DISPENSING ATTACHMENT FOR HAIR DRYERS

[75] Inventor: Charles D. West, Phoenix, Ariz.

[73] Assignee: Christie Ann Deloach, Phoenix, Ariz.

[21] Appl. No.: 517,546

[22] Filed: Aug. 21, 1995

[51] Int. Cl.⁶ .................................................. F26B 21/06
[52] U.S. Cl. ........................................... 34/97; 34/390
[58] Field of Search .......................... 34/283, 96, 97, 34/98, 380, 389, 390

[56] References Cited

U.S. PATENT DOCUMENTS

| | | | |
|---|---|---|---|
| 1,727,212 | 9/1929 | Martin | 34/72 |
| 4,383,377 | 5/1983 | Crafton | 34/60 |
| 4,597,191 | 7/1986 | Juzefczyk | 34/97 |
| 4,835,879 | 6/1989 | Egelstad | 34/97 |
| 5,157,757 | 10/1992 | McDougall | 34/97 |
| 5,241,974 | 9/1993 | Tsai | 34/97 |
| 5,287,635 | 2/1994 | Chan | 34/97 |
| 5,333,787 | 8/1994 | Smith et al. | 34/97 |
| 5,433,017 | 7/1995 | Brauchli et al. | 34/97 |

*Primary Examiner*—Edward K. Look
*Assistant Examiner*—Mark Sgantzos
*Attorney, Agent, or Firm*—Gregory J. Nelson

[57] ABSTRACT

A fragrance dispenser attachable to the barrel of a hair dryer having a housing which is engageable to the hair dryer barrel. A replaceable fragrance-emitting element is contained within the dispenser. The warmed air flow from the dryer releases the fragrance. Various types of elements in a selection of scents may be provided. The dispenser also allows the user to attach conventional accessories to the outlet of the dispenser attachment. Another embodiment has a regulator for controlling the emission of fragrance into the air flow.

13 Claims, 2 Drawing Sheets

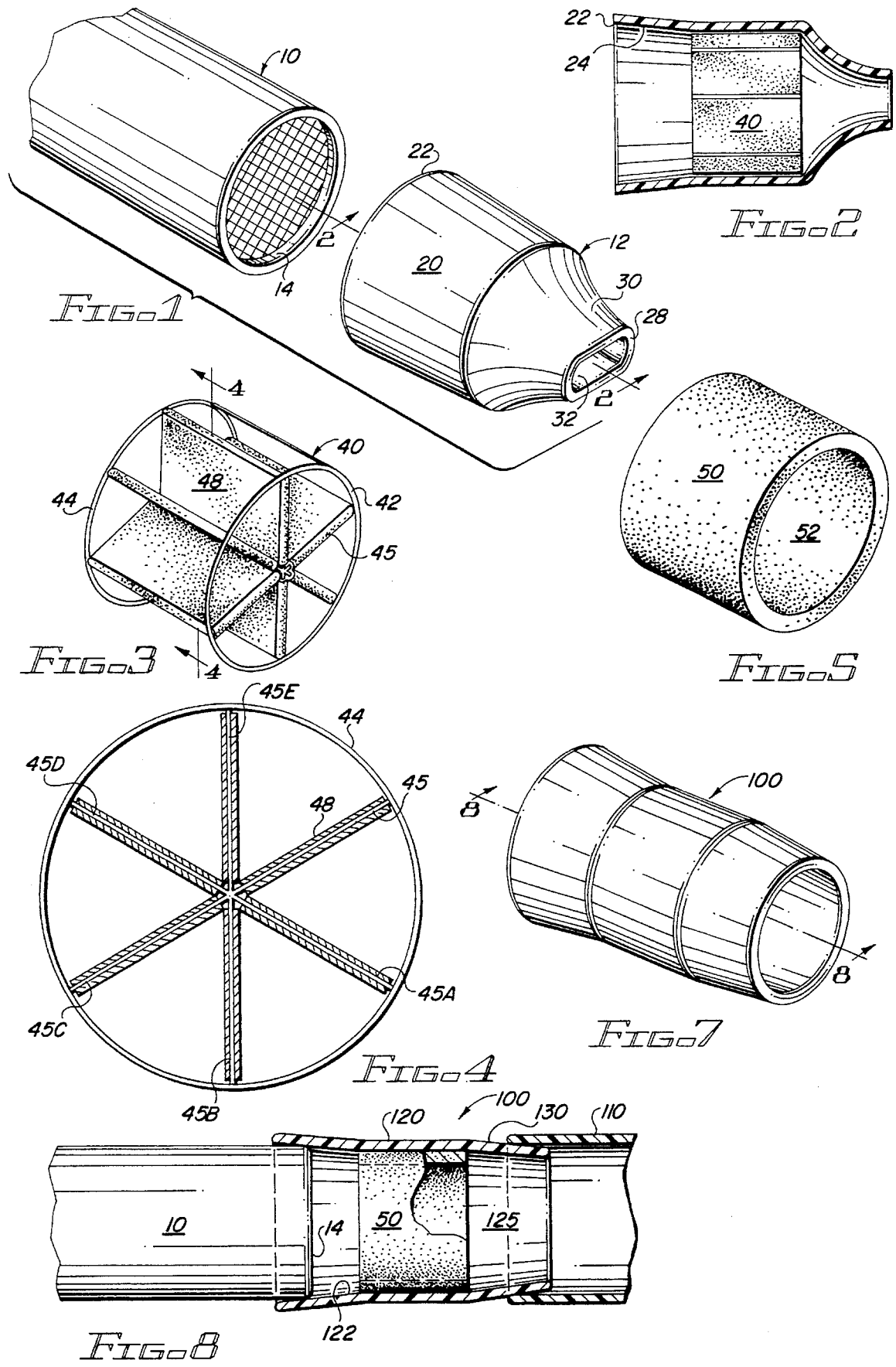

5,572,800

1

AIR FRESHENER DISPENSING ATTACHMENT FOR HAIR DRYERS

FIELD OF THE INVENTION

The present invention relates to an air freshener and more particularly relates to an attachment which may be placed on the discharge end of the barrel of a conventional hair dryer which air freshener contains a deodorizing element which vaporizes to release a fragrance into the air flow. The fragrance may be used to freshen the user's hair or as a room deodorizer.

BACKGROUND OF THE INVENTION

Hair dryers are a common appliance used both in households and professionally by hair stylists to dry and style hair. Hair dryers are available in various makes and models which are generally similar in construction typically having a handle which is grasped by the user and which handle usually includes an off/on switch, fan speed and temperature controls. The housing attached to the handle contains a fan and a heating element. The heated air is discharged by the fan through an elongate barrel terminating at an air discharge. In use, the user holds the dryer by the handle and selects the desired temperature and air flow and directs the heated air onto the hair to dry the hair.

It is also known to utilize self-contained air freshening or deodorizing apparatus which have a housing containing a fan which operates to distribute a vaporized product into the air. Generally these devices are installed in isolated locations where a suitable deodorizing air flow may be established.

Air fresheners of the general type are shown in U.S. Pat. Nos. 5,126,078; 5,223,182; and 5,147,582.

Thus, while air fresheners with air movement generating mechanisms are known and hair dryers are known, it is not known heretofore to provide a conventional hair dryer with means to provide a flow of scented or deodorizing air.

Accordingly, it is a broad object of the present invention to provide an attachment which will fit most standard hair dryers which, when the hair dryer is activated, will release a fragrance or deodorizer into the air flow.

It is another broad object of the present invention to provide a device for delivering fragrance to the hair of the user.

It is still another object of the present invention to provide a convenient device for freshening or fragrancing hair, Still another object of the present is to provide a fragrancing and deodorizing attachment for hair dryers which attachment is adaptable to most conventional hair dryers.

It is still another object of the present invention to provide an attachment adaptable to most conventional hair dryers which produces a fragrance and which allows the user to use the hair dryer as an air distribution device for deodorizing an area.

It is another object of the invention to provide a deodorizing and fragrance emitting attachment for hair dryers which allows the user to ***

BRIEF SUMMARY OF THE INVENTION

Briefly, in a preferred embodiment, the air freshener and fragrance dispenser attachment of the present invention has a cylindrical body with an inlet at one end and an outlet at one end. The inlet end of the body is slightly divergent so that the attachment may be frictionally engaged about the end of the barrel of a hair dryer and will fit most dryers of different makes and models. The attachment contains a replaceable fragrance element which includes a vaporizable material which, as the air from the hair dryer passes through the cartridge, will release a scent into the air stream. The element may be in various configurations and provided in various fragrances and scents.

In an alternate embodiment of the invention, the attachment has a cylindrical body with a tapered inlet end which frictionally engages the end of the barrel of the dryer. The opposite or outlet end of the attachment is configured to receive an appliance such as a conventional air diffuser attachment for a hair dryer. The attachment houses an element such as a replaceable cartridge which includes a vaporizable fragrance releasing material.

In yet another embodiment the fragrance containing attachment is adjustable to control the emission of the fragrance.

BRIEF DESCRIPTION OF THE DRAWINGS

The above and other objects and advantages of the present invention will be more fully understood from the following description, claims and drawings in which:

FIG. 1 is a perspective view showing the barrel of a conventional hair dryer and the fragrance-containing attachment of the present invention;

FIG. 2 is a sectional view taken along line 2—2 of FIG. 1;

FIG. 3 is a perspective view of one embodiment of a replaceable fragrance element;

FIG. 4 is a sectional view taken along line 4—4 of FIG. 3;

FIG. 5 is a perspective view of an alternate embodiment of a fragrance element according to the present invention;

FIG. 7 is a perspective view of an alternate embodiment of the attachment;

FIG. 8 is a sectional view of the attachment shown in FIG. 7, showing the attachment positioned on the barrel of a hair dryer and having a representative conventional hair dryer diffuser secured at the discharge end;

Figure 6:
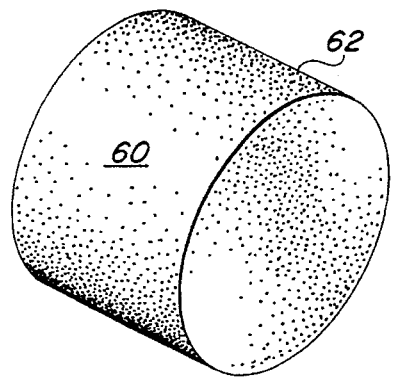
FIG. 6 is a perspective view of yet another embodiment of the replacement fragrance element which may be utilized with the attachment of the present invention.

Turning now to the drawings, particularly FIGS. 1 to 4, the barrel 10 of a conventional hair dryer is shown. The hair dryer forms no part of the present invention but is shown to assist in understanding the present invention since the attachment 12 is specifically intended to be secured to the barrel of the hair dryer as represented by the numeral 10. Hair dryers are of known construction having a handle with selector switches for on/off, level of heat and desired air flow. The housing contains a fan and a heating element and a flow of warm air is discharged at the discharge end 14 of the barrel 10. The details of the construction of a conventional hair dryer are well known and need not be set forth in further detail.

The attachment 12 of the present invention is detachably securable at the end of the barrel of the hair dryer and provides a quick and convenient way of freshening or fragrancing the hair or also may serve as a means of dispensing a room deodorizer. The attachment 12 has a cylindrical body section 20 of suitable heat resistant plastic such as ABS or styrene. The inlet end 22 of the body 20 of the attachment diverges slightly at 24 so that the interior of the inlet 22 may be secured over the exterior of the end of the barrel 10 of the dryer. The taper 24 allows the attachment to be detachably secured to dryer barrel 10 and accommodates dryers having barrels of different configurations. Once the attachment 12 is engaged over the end of the barrel of the dryer, it is secured by a frictional fit. The outlet end 28 of the attachment has a converging wall 30 which terminates at a reduced area nozzle 32. The reduced area nozzle will result in air flow of increased velocity. However, the outlet section of the attachment can be provided in any convenient size or shape depending upon the requirements of the user.

The main body section 20 of the attachment receives a fragrance element 40 as best seen in FIGS. 2 and 3. The element 40 is a replaceable cartridge and has a frame of wire or other heat-resistant material. The frame consists of spaced-apart circular elements 42 and 44 having a diameter slightly less than the internal diameter of the body 20 of the attachment. Multiple panels or ribs of wire mesh 45 to 45E extend diametrally between the circular rings 42 and 44. The wire mesh ribs provide a substrate for a coating 48 of vaporizer freshening or deodorizing material. The vaporizable material 48 is solid or semi-solid and as air current passes across it will cause the material to vaporize releasing a scent or deodorizer into the air stream. When the vaporizable material is expended, the element may be removed or replaced with another element. Similarly, the user may be provided a selection of elements providing different scents or fragrances and may select the desired scent. Various vaporizable materials for releasing a deodorant or fragrance are well known to those in the art, which materials are environmentally acceptable. For example, those materials used in the solid deodorizers of the type sold under the name and mark GLADE PLUG INS Room Deodorizer will work well for this purpose.

Another form of replaceable element is shown in FIG. 5. In this embodiment, the cartridge 50 is generally annular having a diameter closely approximating the interior diameter section 20 of the attachment. Similarly, the overall length of the element 50 is selected to fit into the body at the attachment. The element 50 can be molded of a suitable porous material which will distribute and vaporize the product in the air passing through the annulus 52. Again, the element may be molded from a variety of known products and may be provided to the user in a variety of scents.

In FIG. 6, yet another embodiment of the fragrance element is shown generally designated by the numeral 60. In this embodiment, the cartridge is a generally solid cylindrical cartridge having an outer diameter 62 which is slightly less than the interior diameter of the body 20 of the attachment 12. The element 60 is formed from a porous vaporizable material and which will release the desired scent. The cartridge 60 is formed having sufficient porosity so as not to substantially impede air flow through the element. As the warm air flows through the element, the vaporizable product will be distributed into the air passing therethrough.

In use, the user will select an element such as the element shown in any of the FIGS. 5, or 6, having the desired scent. The element is inserted into the attachment 12 through the inlet end and the element will seat in the position shown in FIG. 2 and represented by the numeral 40 abutting the outlet of the attachment. The attachment 12 is then frictionally engaged over the end of the barrel 10 by forcing the barrel into the inlet 22 of the attachment. The user will then operate the hair dryer in a normal manner, causing a flow of air to be discharged from the hair dryer which air flow may be heated to a desired temperature as determined by the user. The flow of air discharged from the hair dryer will pass through the internal passageway in the attachment 12 from the inlet to the outlet, passing through the fragrance cartridge. Vaporized, fragranced product will be distributed into the air and this fragrance may be directed with the air stream to the hair of the user. As the warm air travels through the element, it activates release of the fragrance which will permeate the hair of the user leaving the desired pleasant scent.

Alternatively, a room deodorizer element may be selected and inserted into the attachment. The hair dryer may then be used as a means of distributing the desired deodorizing scent into a room such as a bathroom.

The primary advantage of the present invention is that it allows the user to apply a pleasant fragrance to the user's hair without the user having to wash his or her the hair with a fragrance shampoo or apply a fragrancing rinse. Also, the hair freshener attachment may be used during normal drying after washing the hair which accomplishes both drying and the fragrance application in a single operation.

Turning now to FIGS. 7 and 8, an alternate embodiment of the attachment of the present invention is shown which is generally designated by the numeral 100 which is both an attachment and an adaptor. Again, the barrel of a conventional hair dryer is shown and designated by the numeral 10. In this embodiment a modified form of the attachment is shown which allows the user to insert the attachment on the end of a conventional hair dryer and still use various other attachments 110. For example, the conventional hair dryer is often provided with various accessories such as attachment 110 which may be a diffuser which, when attached, moderates the strong flow of warm air from the hair dryer. Thus, for certain hair styles, the user may select a diffuser 110 as an attachment to the air outlet of the air dryer which will diffuse and soften the air flow.

The attachment 110 has a body 120 of heat-resistant material. The body 120 has a slightly divergent inlet end 122 which will accommodate insertion of the barrel 10 of dryers having different diameters. The discharge end 130 of the attachment 100 is shown as being slightly convergent so that it may be inserted into the end of a selected accessory 110. The attachment defines a passageway 125 which will receive a selected scent element which is represented by element 50 which is of the type shown in FIG. 5. The element seats in the passageway against the discharge end and will be held in place by the shoulder formed at the intersection between the intermediate body section and the discharge end. The operation of the device is described above with the warmed air from the dryer emanating from the barrel releasing the fragrance and becoming scented as it passes through the element 50. The scented air then passes on to the hair dryer attachment 110 to be applied to the hair of the user.

Figure 11:
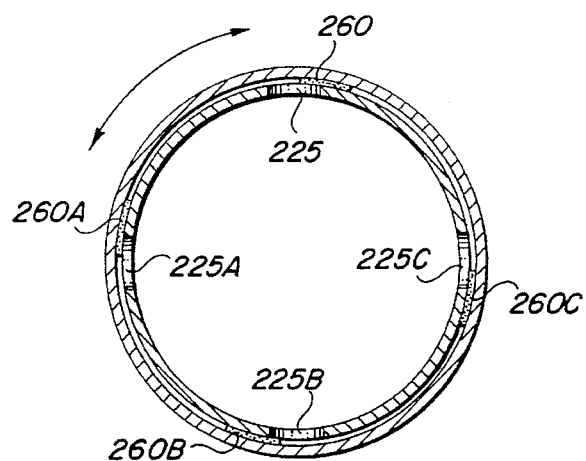
FIG. 11 is a sectional view taken along lines 11—11 of FIG. 10.
Figure 9:
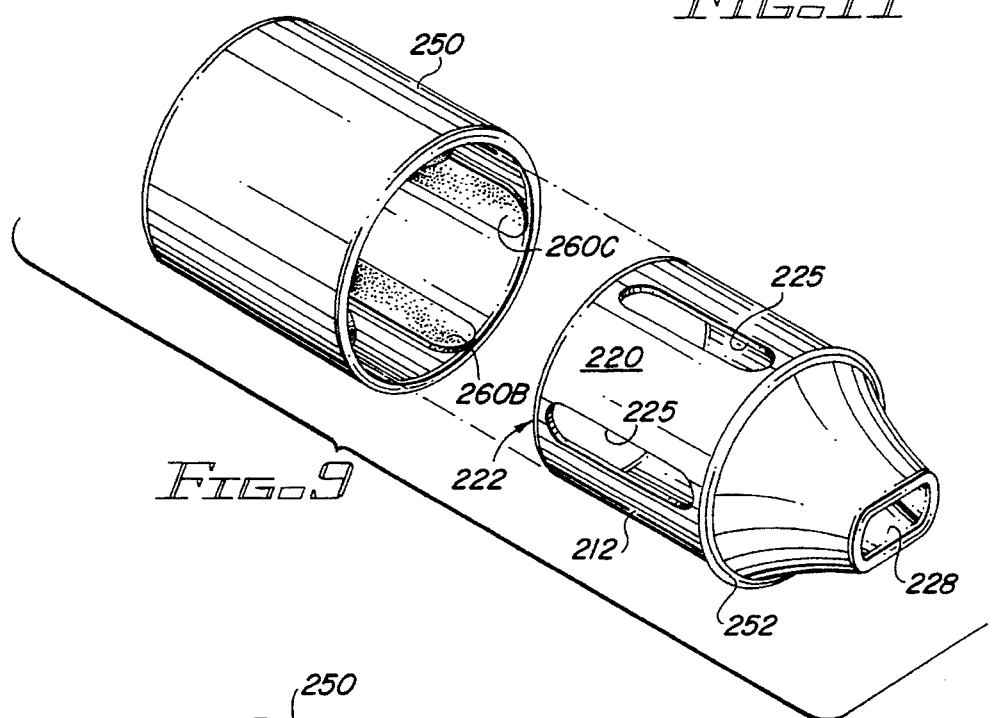
FIG. 9 is an exploded view of yet another embodiment of the present invention.
Figure 10:
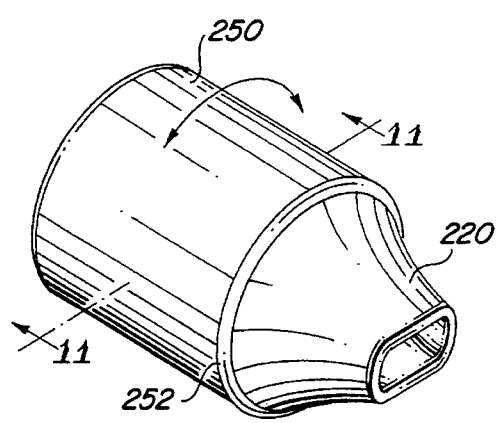
FIG. 10 is a perspective view of the embodiment shown in FIG. 9.

FIGS. 9, 10 and 11 illustrate still another embodiment which permits the user to adjust the attachment to regulate the emission of fragrance. An attachment is similar in construction to that shown in FIGS. 1 and 2 having a body 220 with an inlet 222 which is engageable at the end of a hair dryer barrel, not shown. The outlet 228 defines a nozzle for discharge of scented air.

A plurality of longitudinally extending apertures 225 to 225C extend in body 220. Regulation ring 250 is slidable about body 220 and when engaged about body 220 abuts flange 252. Ring 250 is rotatable to bring scent strips 260–260C in and out of registry with apertures 225–225C to expose the desired area of the scent strips to the apertures thereby regulating the emission of fragrance into the air. The rotational position of the ring 250 can also be selected to de-activate the device by positioning the scent strips in the land areas intermediate the apertures. This will effectively seal off the scent strips from the air flow through the body 220.

While the above discloses what is considered to be the preferred embodiments of the present invention, it is understood that various changes, alterations, modifications may be made to the invention without departing from the spirit and scope of the appended claims. They are intended to be encompassed therein.

I claim:

1. An air freshening dispenser for attachment to a hair dryer of the type having a barrel terminating at an air flow discharge, said dispenser comprising:
   (a) a housing having an inlet and an outlet with an air passage therebetween;
   (b) said inlet having means to detachably secure said housing at the discharge of said hair dryer barrel; and
   (c) fragrance element means insertable in said passage, said fragrance element means including a vaporizable material which will release a fragrance into an airstream passing from the inlet to the outlet through said air passage.

2. The air freshening dispenser of claim 1 wherein said dispenser has a generally cylindrical body with inlet having a generally tapering section.

3. The air freshening dispenser of claim 2 further including a nozzle of reduced diameter at said housing outlet.

4. The air freshening dispenser of claim 1 wherein said element is a generally porous member comprised of vaporizable fragrance releasing material.

5. The air freshening dispenser of claim 1 wherein said outlet has means associated therewith to detachably secure a hair dryer attachment thereto.

6. The air freshening dispenser of claim 1 wherein said housing is molded from a rigid plastic material.

7. The air freshening dispenser of claim 1 wherein said means associated with said outlet comprises a tapered section.

8. The air freshening dispenser of claim 1 further including means for regulating the area of the fragrance element exposed to the said air stream.

9. An air freshening dispenser for attachment to a hair dryer of the type having a barrel terminating at an air flow discharge, said dispenser comprising:
   (a) a housing having an inlet and an outlet with an air passage therebetween for receiving the air flow from the dryer;
   (b) said inlet having means to detachably secure said housing to the discharge of the hair dryer; and
   (c) regulating means including a fragrance element, said regulating means being adjustable relative to said housing to regulate the emission of fragrance carried by said air flow in said air passage and discharged at said outlet of said attachment.

10. The air freshening dispenser of claim 9 wherein said housing defines an aperture therein and said regulating means comprises a ring rotative relative to said housing to selectively bring the fragrance element into and out of registry with said aperture.

11. The air freshening dispenser of claim 10 including a plurality of apertures defined by said housing and a plurality of fragrance elements.

12. An air freshening dispenser for attachment to a hair dryer of the type having a barrel terminating at an air flow discharge, said dispenser comprising:
   (a) a housing having an inlet and an outlet with an air passage therebetween for receiving the air flow from the hair dryer;
   (b) said inlet having means to detachably secure said housing at the discharge of said hair dryer barrel; and
   fragrance element means insertable in said air passage, said fragrance element means including a vaporizable material which will release a fragrance into an airstream passing from the inlet to the outlet through said air passage, said fragrance element means including a frame having a plurality of generally radially extending ribs, said ribs having said vaporizable material associated therewith.

13. An air freshening dispenser for attachment to a hair dryer of the type having a barrel terminating at an air flow discharge, said dispenser comprising:
   (a) a housing having an inlet and an outlet with an air passage therebetween for receiving the air flow from the hair dryer;
   (b) said inlet having means to detachably secure said housing at the discharge of said hair dryer barrel;
   (c) fragrance element means insertable in said air passage, said fragrance element means including a vaporizable material which will release a fragrance into an airstream passing from the inlet to the outlet through said air passage; and
   (d) means for regulating the area of the fragrance element exposed to the said air flow.

\* \* \* \* \*